United States Patent
Weinberg et al.

(10) Patent No.: US 8,076,088 B2
(45) Date of Patent: Dec. 13, 2011

(54) METHOD OF DETECTING HUMAN β-DEFENSINS

(75) Inventors: Aaron Weinberg, Shaker Heights, OH (US); Santosh K. Ghosh, Mayfield Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 347 days.

(21) Appl. No.: 12/390,890

(22) Filed: Feb. 23, 2009

(65) Prior Publication Data

US 2010/0022025 A1    Jan. 28, 2010

Related U.S. Application Data

(60) Provisional application No. 61/030,688, filed on Feb. 22, 2008.

(51) Int. Cl.
*G01N 33/53* (2006.01)
(52) U.S. Cl. ........ 435/7.1; 435/7.92; 435/962; 436/501; 436/825
(58) Field of Classification Search .................. None
See application file for complete search history.

(56) References Cited

U.S. PATENT DOCUMENTS

2007/0093416 A1 *  4/2007  Igarashi et al. ................. 514/12

OTHER PUBLICATIONS

Ghosh et al., Quantification of Human B-Defensin- and -3 in Body Fluids: Application for Studies of Innate Immunity, Clinical Chemistry 53:4 Apr. 2007, pp. 757-765.*

Yin et al., Mouse salivary glands and human B-defensin-2 as a study model for antimicrobial gene therapy: technical considerations, International Journal of Antimicrobial Agents 28, 2006, pp. 352-360.*

* cited by examiner

*Primary Examiner* — Melanie J Yu
*Assistant Examiner* — Gary W Counts
(74) *Attorney, Agent, or Firm* — Tarolli, Sundheim, Covell & Tummino LLP

(57) ABSTRACT

A method of detecting β-defensin in a bodily sample from a subject includes reducing the electrostatic interaction between β-defensin and negatively charged moieties in the bodily sample prior to detecting the β-defensin with an antibody or epitope binding fragment thereof.

20 Claims, 9 Drawing Sheets

METHOD OF DETECTING HUMAN β-DEFENSINS

RELATED APPLICATION

This application claims priority from U.S. Provisional Application No. 61/030,688, filed Feb. 22, 2008, the subject matter, which is incorporated herein by reference.

GOVERNMENT FUNDING

This invention was made with government support under Grant Nos. RO1 DE 16334, RO1 DE 17334 and RO1 DE 15510 awarded by the National Institute of Health. The United States Government has certain rights in the invention.

FIELD OF INVENTION

The present invention relates to a method of detecting β-defensin in a bodily sample from a subject and particularly relates to an immunoassay for detecting and quantifying human β-defensin in a bodily sample from a subject.

BACKGROUND OF THE INVENTION

Antimicrobial peptides have been identified as key components in innate host defense and as important contributors in maintaining health at mucosal barriers. Human β-defensins, a family of epithelial cell-derived cationic peptides (4-5 kDa), are known to exhibit both antimicrobial and immunomodulatory properties (Harder et al., (1997) Nature 387: 861; Harder et al., (2001) J. Biol. Chem. 276:5707-13; Bowdish et al., (2006) Curr. Top. Microbiol. Immun. 306:27-66). Four human β-defensins have been identified thus far. Human β-defensins 1 (hBD-1) is constitutively expressed, whereas hBD-2 and -3 are inducible (Harder et al., (2001); Krasanaprakornkit et al., (1998) Infect. Immun. 66:4222-4228; Garcia et al., (2001) Cell Tissue Res. 306:257-264). All 3 peptides can be isolated from mucosal sites of the body. An hBD-4 transcript has also been described (Garcia et al. (2001) FASEB J. 15:1819-1821; Xu et al., (2006) Appl. Microbiol. Biotechnol. 72:471-479). hBDs have demonstrated activity against gram-positive and gram-negative bacteria, mycobacteria, fungi, and certain enveloped viruses at low micromolar concentrations (Yadava et al., (2006) Int. J. Antimicrob Agents 28:132-137; De Smet and Contreras (2005) Biotechnol. Lett 27:1337-1347). We recently showed that hBDs have antiretroviral activity by inhibiting HIV-1 infectivity of immunocompetent cells (Quinones-Mateu et al., (2003) Aids 17:F39-48; Feng et al., (2006) J. Immunol. 177:782-786). In addition, hBDs can enhance adaptive immunity by acting as adjuvant and chemoattracting T cells, immature dendritic cells, B cells, neutrophils, and macrophages (Yang et al., (1999) Science 286:525-528; Tani et al., (2000) Int. Immunol. 12:691-700; Oppenheimer et al., (2003) 62(Supp2); ii17-21). With new information emerging about these pluripotent peptides and their role in mucosal protection, diagnostic tools to quantify inducible β-defensins in body fluids and tissues are essential to better associate β-defensin expression with disease predisposition and progression.

Previous methods of quantifying human β-defensins in body fluids involved acid extraction followed by slot blot assays (Sahasrabudhe et al., (2000) 79:1669-1674; Tao et al., (2005) Antimicrob. Agents Chemother. 49:3883-3888), semiquantitative Western analysis (Mathews et al., (1999) 67:2740-2745; Chen et al., (2004) J. Cyst. Fibros. 3:45-50; Ross et al., (2004) Transplantation 78:1222-1224), or RIA (Hiratsuka et al., (2003) Thorax 58:425-430).

SUMMARY

The present invention relates to a method of detecting β-defensin in a bodily sample of a subject. The method includes obtaining a bodily sample from a subject. The electrostatic interaction between β-defensin and negatively charged moieties in the bodily sample is then reduced. The bodily sample is contacted with a capture antibody or an epitope binding fragment thereof. The capture antibody or an epitope binding fragment thereof is immunoreactive with the β-defensin and binds to the β-defensin. The β-defensin bound to the capture antibody is then detected. The bound β-defensin can be detected by contacting the bound β-defensin with a detection antibody or epitope binding fragment thereof. The detection antibody or epitope binding fragment thereof is coupled to a detectable label. The detectable label can then detected.

The present invention also relates to a method of quantifying β-defensin in a subject. The method includes obtaining a bodily sample from a subject. The electrostatic interaction between β-defensin and negatively charged moieties in the bodily sample is then reduced. The bodily sample is contacted with a capture antibody or an epitope binding fragment thereof. The capture antibody or an epitope binding fragment thereof is immunoreactive with the β-defensin and binds to the β-defensin. The bound β-defensin is contacted with a detection antibody or epitope binding fragment thereof. The detection antibody or epitope binding fragment thereof is coupled to a detectable label. The detectable label in the bodily sample is then detected. The amount of detectable label in the sample is correlated to an amount of β-defensin in the bodily sample.

DETAILED DESCRIPTION

Figure 1:
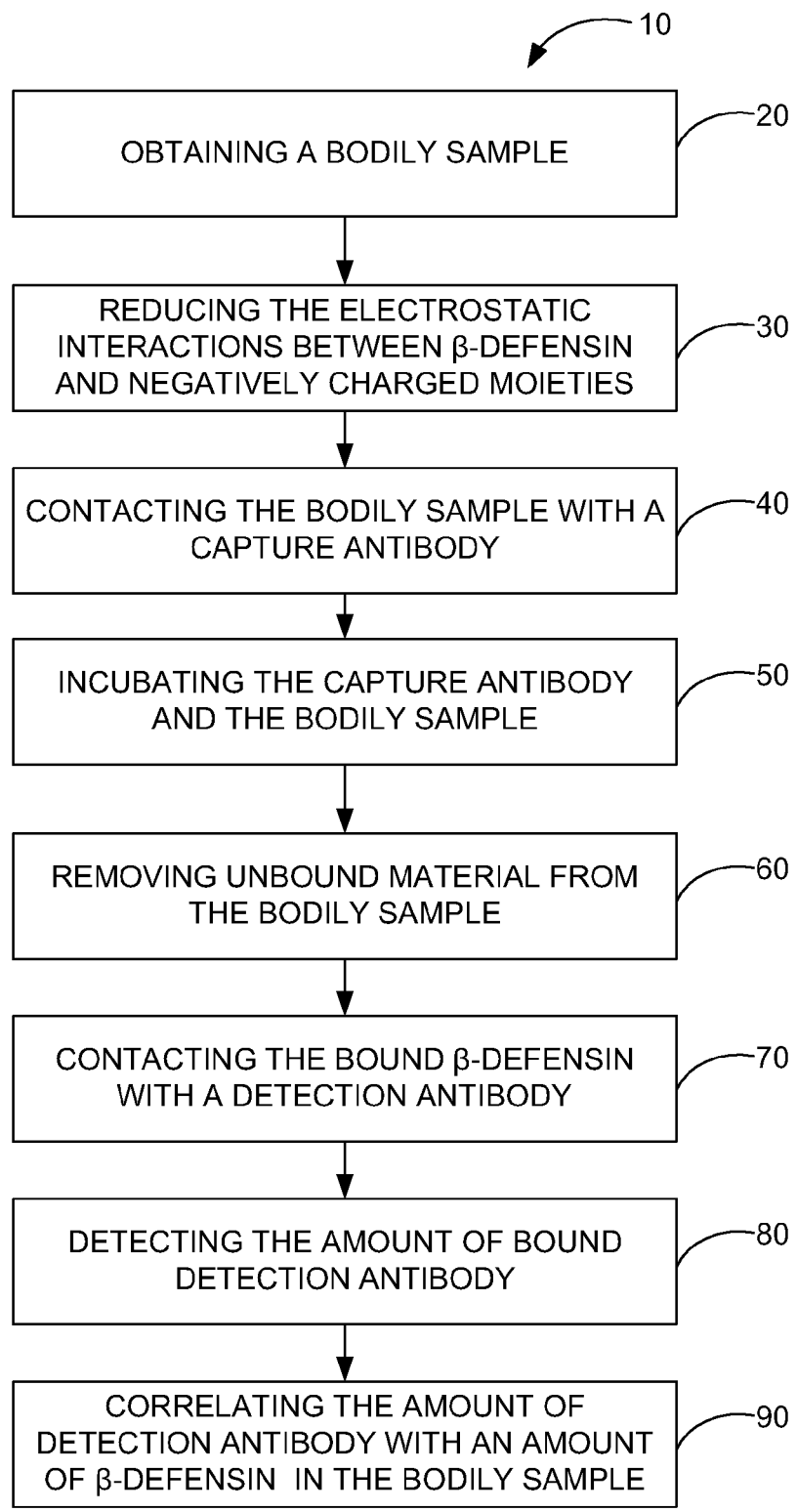
FIG. 1 illustrates a schematic flow diagram of a β-defensin quantification method in accordance with an aspect of the invention.

The present invention relates to a method of detecting and/or quantifying β-defensin in a bodily sample from a subject. The term "β-defensin" as used herein refers to the family of epithelial cell-derived cationic peptides (4-5 kDa), which exhibit both antimicrobial and immunomodulatory properties. More specifically "β-defensin" as used herein refers to inducible members of the β-defensin family (e.g., β-defensin 2, β-defensin 3, and β-defensin 4). The term "inducible" refers to those β-defensin family member proteins whose expression increases in response to a signal in a given environmental background.

The method uses an immunoassay to detect and/or quantify β-defensin in bodily samples that contain β-defensin masking agents. It was found that bodily samples, such as epithelial cell derived fluids (e.g., saliva), contain negatively charged moieties, such as anionic glycoproteins that can mask antibody detection of β-defensin and inhibit β-defensin detection and quantification. The immunoassay of the present invention can overcome the masking effects of the masking agents and provide an accurate method for detecting and quantifying β-defensin in bodily samples, such as saliva.

The term "detection" or "detecting" in accordance with the present invention is used in the broadest sense to include both qualitative and quantitative measurements of β-defensin. In one aspect, the detecting method as described herein is used to identify the mere presence of β-defensin in a subject's bodily sample.

Various immunoassays may be employed as a proper β-defensin detection means and are well-known in the art. Examples of the immunoassays include sandwich methods employing a monoclonal antibody and another monoclonal antibody as primary and secondary antibodies, respectively, sandwich methods employing a monoclonal antibody and a polyclonal antibody as primary and secondary antibodies, sandwich methods employing the polyclonal antibody and a polyclonal antibody as primary and secondary antibodies.

The term "antibody" is used in the broadest sense and includes polyclonal antibodies, monoclonal antibodies, and epitope binding antibody fragments thereof so long as they exhibit the desired binding specificity.

The term "monoclonal antibody" or "monoclonal antibodies" as used herein refers to a preparation produced by one type of immune cell that are all clones of a single parent cell typically including identical antibodies directed against a single epitope.

The term "polyclonal antibody" or "polyclonal antibodies" as used herein refers to a preparation typically including different antibodies directed against multiple epitopes. The modifier "polyclonal" indicates that character of the antibody as being obtained from a heterogenous population of antibodies, and is not to be construed as requiring production of the antibody by any particular method.

In a specific example, polyclonal antibodies used in the present invention can be obtained commercially (see examples below) or can be produced by one skilled in the art. Polyclonal antibodies for use in the present invention can be prepared by immunizing an appropriate animal with a β defensin protein, optionally coupled to KLH or to albumin and/or combined with an appropriate adjuvant such as (complete or incomplete) Freund's adjuvant or aluminum hydroxide; after obtaining a satisfactory antibody titer, the antibodies are harvested by collecting serum from the immunized animals and can then be enriched with IgG by precipitation and/or purified by affinity chromatography according to conventional techniques.

FIG. 1 is a schematic flow diagram illustrating an immunoassay method 10 of detecting β-defensin in accordance with one aspect of the present invention. In the method 10, at 20, a bodily sample suspected of containing β-defensin is obtained from the subject. The term "bodily sample", as used herein, refers to a body sample from any subject. The subject can be a mammal, and is preferably a human. Bodily samples may be obtained or collected by any manner known to those skilled in the art. Bodily samples may include any bodily sample from which one skilled in the art would desire the detection or quantification of β-defensin and particularly, bodily samples that contain β-defensin masking agents. Samples can include biological fluids, such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, genital secretions, cervicovagianal lavage, bronchioalveolar lavage, blister fluid, mucus, tissue culture medium, tissue extracts, such as homogenized tissue, and cellular extracts, as well as any other epithelial cell derived fluid. By way of example, the bodily fluid can be selected from the group consisting of saliva, genital secretions cervicovaginal lavage, bronchioalveolar lavage, blister fluid, mucous, and combinations thereof.

At 30, an agent is added to the bodily sample that reduces electrostatic interaction between β-defensin and negatively charged moieties in the bodily sample without affecting binding of detection antibodies and/or fragments thereof to the β-defensins. Negatively charged moieties in the bodily sample can include anionic glycoproteins, such as mucins, a family of large, heavily glycosylated proteins, and calprotectin, a calcium-binding protein secreted predominantly by neutrophils.

The agent can include a positively charged moiety and/or ions capable of reducing the electrostatic interaction between β-defensin and negatively charged moieties in the bodily sample. The positively charged moiety and/or ions can be provided in the bodily sample by administering a salt to the bodily sample that upon addition can readily dissociate and form cations or positively charge electrolytes that are capable of associating with the negatively charged moieties. In one example, the salt upon dissociation can form divalent cations capable of associating with the negatively charged moiety. Examples of salts capable of forming divalent cations are $MgCl_2$ and $CaCl_2$. $MgCl_2$ and $CaCl_2$ upon addition to a bodily sample can dissociated and form $Mg^{2+}$ and $Ca^{2+}$ cations.

The agent can be added to the bodily sample at an amount effective to reduce electrostatic interaction between β-defensin and negatively charged moieties in the bodily sample without affecting binding of detection antibodies and/or fragments thereof to the β-defensins. By way of example, the electrostatic interaction between β-defensin and negatively charged moieties in the bodily sample can be reduced by adding $CaCl_2$ to a bodily sample at a concentration of about 50 mmol/L to about 500 mmol/L. Positively charged moieties can be added to the bodily sample before antibodies are contacted with the bodily sample and/or simultaneously with capture antibody contact.

At 40, following and/or simultaneously with the contacting of the bodily sample with the positively charged moieties, the bodily sample can be contacted with a capture antibody that is known to be immunoreactive with, and/or bind to one or more binding epitopes of the β-defensins in the bodily sample.

The term "capture antibody" or "capture antibodies", as used herein, refers to an antibody that is capable of binding and capturing β-defensin in a sample such that under suitable conditions, the capture antibody-β-defensin complex can be separated from the rest of the sample. The capture antibody can include known antibodies that are capable of selectively binding to β-defensin. Such antibodies can be, for example: hBD-2 antibodies, which are commercially available from Peprotech, Rocky Hill, N.J., USA, Cell Sciences, Canton, Mass., USA, and Alpha Diagnostics, San Antonio, Tex., USA; and, hBD-3 antibodies, which are commercially available from Orbigen, San Diego, Calif., USA, Genetech, South San Francisco, Calif., USA, and Peprotech, Rocky Hill, N.J., USA.

Typically, the capture antibody can be immobilized or immobilizable. The capture antibody can be immobilized on a solid phase by insolubilizing the capture-antibody before a detection or quantification procedure, as described herein. Immobilization may occur by adsorption to a water-insoluble matrix or surface (U.S. Pat. No. 3,720,760, herein incorporated by reference in its entirety) or non-covalent or covalent coupling, for example, using glutaraldehyde or carbodiimide cross-linking, with or without prior activation of the support with, e.g., nitric acid and a reducing agent as described in U.S. Pat. No. 3,645,852 or in Rotmans et al., J. Immunol. Methods 57:87-98 (1983)), or afterward, such as by immunoprecipitation.

The solid phase used for immobilization may be any inert support or carrier that is essentially water insoluble and useful in immunometric assays, including supports in the form of, for example, surfaces, particles, porous matrices, etc. Examples of commonly used supports include small sheets, Sephadex, polyvinyl chloride plastic beads, and assay plates or test tubes manufactured from polyethylene, polypropylene, polystyrene, and the like including 96-well microtiter plates and 384-well microtiter well plates, as well as particulate materials, such as filter paper, agarose, cross-linked dextran, and other polysaccharides.

Alternatively, reactive water-insoluble matrices, such as cyanogens bromide-activated carbohydrates and the reactive substrates described in U.S. Pat. Nos. 3,969,287; 3,691,016; 4,195,128; 4,247,642; 4,229,537; and 4,330,440 are suitably employed for capture-antibody immobilization. In one example, the immobilized capture antibodies are coated on a microtiter plate, and in particular the preferred solid phase used is a multi-well microtiter plate that can be used to analyze several samples at one time. For example, the multi-well microtiter plate can be a microtest 96-well ELISA plate, such as those sold by Nune, Maxisorb, or Immulon.

The solid phase is coated with the capture antibody, which may be linked by a non-covalent or covalent interaction or physical linkage as desired. Techniques for attachment include those described in U.S. Pat. No. 4,376,110 and the references cited therein. If covalent binding is used, the plate or other solid phase can be incubated with a cross-linking agent together with the capture reagent under conditions well known in the art.

Commonly used cross-linking agents for attaching the capture antibody to the solid phase substrate include, e.g., 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Deriving agents, such as methyl-3-[(p-azidophenyl)dithio]propioimidate yield photoactivatable intermediates capable of forming cross-links in the presence of light.

If micro-titer well plates (e.g., 96-well plates or 384-well plates) are utilized, they can be coated with antibodies (typically diluted in a buffer) at, for example, room temperature and for about 2 to about 3 hours. The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriates blocking agents for this purpose include, e.g., gelatin, bovine serum albumin, egg albumin, casein, and non-fat milk.

After coating and blocking, a bodily sample to be analyzed for the detection of β-defensin is added to the immobilized phase. The bodily sample can be appropriately diluted with, for example, a buffer (e.g., phosphate-buffered saline (PBS)), or a lysis buffer (e.g. phosphate-buffered saline (PBS) with 1% Nonidet P-40, 0.5% sodium deoxycholate, 5 mM EDTA, and pH 8.0).

The various reagents for use in the present invention, are prepared and used according to conventional molecular biology and immunology techniques following standard protocols such as those described in Current Protocols in Molecular Biology (Frederick M AUSUBEL, 2000, Wiley and Son Inc., Library of Congress, USA), in Current Protocols in Immunology (John E. Cologan, 2000, Wiley and Son Inc., Library of Congress, USA) and in Antibodies: A Laboratory Manual (E. Howell and D. Lane, Cold Spring Harbor Laboratory, 1988).

For sufficient sensitivity, the amount of bodily sample contacted with the antibodies can be such that the antibodies are in molar excess of the maximum molar concentration of the β-defensin after appropriate dilution of the sample. This anticipated level depends mainly on any known correlation between the concentration levels of the β-defensin in the particular bodily sample being analyzed with the clinical condition of the subject.

At 50, following contact of the bodily sample with the capture antibody or an epitope binding fragment thereof, the composition is incubated. The conditions for incubation of the bodily sample and immobilized antibody are selected by one skilled in the art to maximize sensitivity of the assay and to minimize dissociation.

The incubation can be accomplished at fairly constant temperatures, ranging from about 0 C. to about 40° C., such as room temperature (e.g., about 25° C.). The time for incubation depends primarily on the temperature, being generally no greater than about 10 hours to avoid an insensitive assay. For example, the incubation time can be from about 0.5 to about 3 hours and particularly about 1.5 to about 3 hours at room temperature to maximize binding to the capture antibodies.

Following incubation of the bodily sample, at 60, the bodily sample is separated (preferably by washing) from the antibodies to remove uncaptured proteins and materials of the bodily sample. The solution used for washing is generally a buffer ("washing buffer") with a pH determined using the consideration and buffers typically used for the incubation step. The washing may be done, for example three or more times. The temperature of washing is generally from refrigerator to moderate temperatures, with a constant temperature maintained during the assay period, typically from about 0 to about 40° C. Optionally, a cross-linking agent or other suitable agent may be added at this stage to allow the now-bound protein to be covalently attached to the capture antibodies if there is any concern that the captured proteins may dissociate to some extent in the subsequent steps.

Following separation of the uncaptured materials in the bodily sample, at 70, the capture antibodies (e.g., anti-β-defensin antibody) and captured β-defensin are contacted with detecting antibodies (or epitope biding fragments thereof).

The term "detecting antibody" or "detectable antibody" as used herein, refers to an antibody that is capable of being detected whether directly through a label amplified by a detection means, or indirectly through, e.g., another antibody that is labeled and readily detectable.

The detecting-antibody can be labeled with any detectable functionality or module that does not interfere with the binding of the detecting antibody to free binding epitopes on the bound β-defensins. Examples of labels are those labels known for use in immunoassays, including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, $^{131}I$, fluorophores, such as rare earth chelates or fluorescein and its derivatives, rhodamine and its derivatives, dansyl, umbelliferone, luciferases, e.g. firefly luciferase and bacterial luciferase (U.S. Pat. No. 4,737,456), luciferin, 2,3-dihydrophthalazinediones, horseradish peroxidase (HRP), alkaline phosphitase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HPP, lactoperoxidase, or microperoxidase, biotin/avidin, biotin/streptavidin, biotin/Streptavidin-β-galactosidase with MUG, spin labels, bacteriophage labels, stable free radicals, and the like. Conventional methods are available to bind these labels covalently to proteins or polypeptides. For instance, coupling agents, such as dialdehydes, carbodiimides, dimaleimides, bis-imidates, bis-diazotized benzidine, and the like may be used to tag the antibodies with the above-described fluorescent, chemiluminescent, and enzyme labels (e.g., U.S. Pat. No. 3,940,475 (fluorimetry) and U.S. Pat. No. 3,645,090 (enzymes); Hunter et al Nature 144:945 (1962); David et al. Biochemistry 13:1014-1021 (1974); Pain et al. J. Immunol. Methods 40:219-230 (1981); and Nygren J. Histochem and Cytochem 30:407-412 (1982)).

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay: in Methods in Enzymology, ed. J. J. Langone and H. Van Vunakis, Vol. 73 (Academic Press, New York, N.Y., 1981), pp. 147-166.

A molar excess of the detecting antibody with respect to the maximum concentration of free binding epitopes expected is added to the plate after it is washed.

At 80, the presence of and/or the amount of detectable module is detected. In one example of the present invention, the amount of bound detecting antibody is determined by removing excess unbound detection antibody by washing and then measuring the amount of the attached label using detection methods appropriate to the detectable module or label used (see above). The mere presence of the detectable label used may indicate the presence of β-defensin in the bodily sample. In the case of enzymes, the amount of color developed and measured can be a direct measurement of the amount of β-defensin present in a given sample.

At 90, the amount of detectable module in the bodily sample can be correlated to an amount of β-defensin in a subject's sample. The amount of β-defensin present can be quantified using known ELISA quantification method, such as comparing the detected β-defensin with a standard or by comparing serial diluted samples. The absence of substantially any detectable signal can be indicative of the absence of substantially any β-defensin in a subject's given sample. Conversely, using the methods described herein, the measurement of a detectable signal can be indicative of the presence of β-defensin, the level of the detected signal being proportional to the amount of β-defensin in the subject's bodily sample. The amount of β-defensin in a subject's sample may be further correlated by those having skill in the art to a subject's general fitness or level of β-defensin induction by comparing the amount of β-defensin in a bodily sample to the amounts of β-defensin in control bodily samples.

The following examples are intended to illustrate embodiments now known for practicing the invention, but the invention is not to be considered limited to these examples.

EXAMPLE

Human β-defensins (hBDs) are epithelial cell-derived antimicrobial and immunoregulatory cationic peptides. The main objective of the present study was to develop a sensitive and reproducible analytical tool to measure hBD-2 and hBD-3 peptide concentrations and use it to quantify these peptides in saliva and other body fluids.

We developed sandwich ELISAs using commercially available capture and detection antibodies and determined optimal assay conditions (with 250 mmol/L $CaCL_2$) to overcome masking by endogenous components of body fluids. We used recombinant hBD as calibrators and for recovery testing.

Materials and Methods
Sample Collection

Individuals who contributed saliva samples were chosen at random, with equal representation of male and female participants and reflective of all age groups, from infants to the elderly. We did not exclude anyone for smoking or taking medications. We collected unstimulated saliva samples from infants and young children by use of sterile disposable pipettes, adults were asked to expectorate directly into sterile tubes. Saliva samples were then transferred into sterile vials, centrifuged at 10000 g at 4° C. for 20 min, and stored at −70° C. until use. We obtained blister fluids (BF) from the Skin Diseases Research Center (Department of Dermatology, Case School of Medicine and University Hospitals of Cleveland). Blisters were generated by applying suction blister cups onto forearm sites; after about 90-120 min, the vacuum was released and fluid was aspirated from each blister using a 23-gauge needle. Fluids were microcentrifuged (8000 g) for 5 min, and the supernatants were frozen at −70° C. We collected bronchioalveolar lavage (BAL) fluids from healthy participants as described (Technical recommendations and guidelines for bronchioalveolar lavage (BAL): Report of the European Society for Pneumology Task Group (1989) Eur. Respir. pp. 561-585). We collected female genital secretions from premenopausal women by 2 different procedures. In the first procedure (vaginal swab), we used sterile dry swabs to collect genital secretions on the endocervix. The swabs were gently applied on the cervical os, and a slight pressure was applied by partly rotating the swabs, without any mucosal trauma. The swab samples were rapidly inserted into 1 mL PBS (137 mM NaCl, 10 mM phosphate, 2.7 mM KCl; pH 7.2) and stored at −70° C. until use. After vaginal swab sampling, we collected cervicovagiual lavage (CVL) by use of a standardized 60-s vaginal washing with 10 mL PBS (pH 7.2) as described (Belec et al., (1995) Clin. Diag. Lab Immunol. 57-61).

Generation of Recombinant hBD-2 and hBD-3

We produced recombinant human BD-2 from the infection of Sf21 cells with baculovirus constructs as described (Valore et al., (1998) J. Clin. Invest. 101:1633-1642). We produced recombinant human BD-3 using an hBD-3-His tag fusion construct, generated by PCR and cloned into pET-3Oc (Harder et al., (2001) J. Biol. Chem. 276:5707-5713). We confirmed the identity and purity of rhBD-2 and -3 by acid urea-polyacrylamide gel electrophoresis migration, N-terminal amino acid sequencing, and matrix-assisted laser desorption/ionization time-of-flight mass spectrometry. We have described the use of these peptides in previous work (Quinones-Mateu (2003) Aids 17:F39-48).

Elisa

We coated 96-well immunoplates (MaxiSorp™; Nunc) with 50 μL anti-hBD-2 or -hBD-3 antibodies from different vendors (Table 1), diluted to 1 mg/L in 0.05 mol/L carbonate buffer, pH 9.6, 4° C., for 18 h.

TABLE 1

| Antibodies | Vendors | Hosts |
|---|---|---|
| hBD-2 | Peprotech, Rocky Hill, NJ, USA | Goat |
| | Cell Sciences, Canton, MA, USA | Goat |
| | Alpha Diagnostics, San Antonio | Rabbit |
| hBD-3 | Orbigen, San Diego, CA, USA | Rabbit |
| | Genentech, South San Francisco, CA, USA | Rabbit |
| | Peprotech, Rocky Hill, NJ, USA | Rabbit |

Subsequently, we blocked the wells with 200 μL of 1% bovine serum albumin in PBS at room temperature for 10 min. After washing 3 times with 200 μL PBS containing 1 mL/L TWEEN-20, we incubated 100 μL/well of test samples at room temperature for 60 min. The plates were washed 3 times with PBS containing 1 mL/L TWEEN-20, and wells were incubated at room temperature with 50 μL secondary antibody diluted to 0.2 mg/L in PBS plus 1 mL/L TWEEN-20 for 30 min. Plates were washed 3 times with PBS plus 1 mL/L Tween 20 and filled with 50 μL/well stre ptavidin-peroxtdase (Roche Diagnostics; 1:10 000 in PBS plus 1 mL/L Tween 20). Plates were then incubated at room temperature for an additional 30 min, washed 3 times as described above, and incubated with 2,2'-azino-bis-3-ethylbenzthiazoline-6-sulfonic acid (Roche Diagnostics) in the dark at room temperature for 20 min, Absorbance was measured at 415 nm with a microplate reader (Bio-Rad Model 680).

Unless otherwise mentioned, during the validation and standardization process we performed ELISA assays in 1×PBS (pH 7.3) using antibody pairs from Peprotech. To measure defensin concentrations in body fluids, we performed ELISA using 250 mmol/L CaCl2 (final concentration). We quantified hBDs by simultaneous ELISA runs (in 250 mmol/L CaCl2) using recombinant hBDs as calibrators.

Mucin Isolation: and Modification

Ovine submaxillary gland mucin (OSM) was purified from frozen glands as described (Gerken et al., (1984) Biochemistry 23:1485-1497), omitting the hydroxyapatite chromatographic step and including protease inhibitors CHELEX 100 and phenyl-methane-sulfonylfluoride) in the initial stages of purification, Enzymatic desialylization of OSM (giving a -OSM) was performed as described (Gerken et al., (1984)) using neuraminidase from Ciostridium perfringens (Sigma). [$^{13}$C]NMR spectra confirmed the purity of the isolated mucin and complete removal of the sialic acid after neuraminidase treatment. Note that native OSM contains exclusively the disaccharide α-NeuNAc 2-6 α-GalNAc—O—Ser/Thr and is therefore one of the most heavily sialylated mucins.

Results

Result Summary: hBD-2 and -3 detection limits were about 75 ng/L and about 3 μg/L, respectively. Mean (SD range) values in saliva samples from healthy donors (n=60) were 9.5 (1.2-21) μg/L for hBD-2 and 326 (50-931) μg/L for hBD-3. We did not detect hBD-3 in suction blister fluid (BF; n=10) or bronchioalveolar lavage (BAL; n=5) from healthy participants. We detected low hBD-2 peptide concentrations in BF and BAL, 0.16 (0.03-0.32) and 0.04 (0-0.049) µg/g total protein, respectively. We observed no correlation of hBD-2 in BF and saliva or BAL and saliva from the same person. In vaginal swabs from healthy women (n=2), mean hBD-2 and -3 concentrations were 3.42 and 103 µg/g total protein, respectively. Cervicovaginal lavage from the same women contained mean concentrations of 1.46 and 55.5 µg/g total protein.

Figure 2:
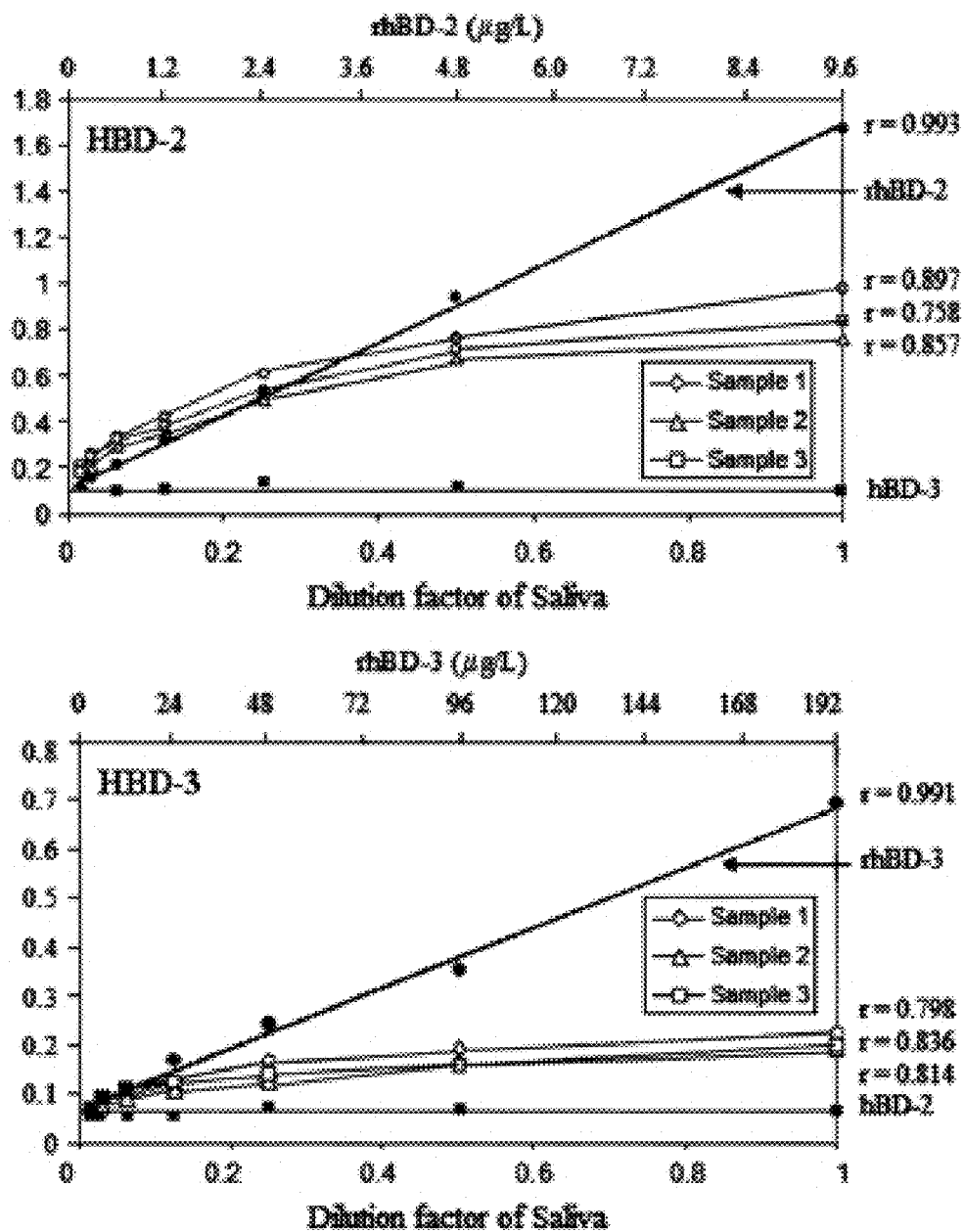
FIG. 2 illustrates plots of ELISA detection of hBD-2 (A) and hBD-3 (B) in serially diluted saliva samples. Saliva samples were serially diluted as indicated with PBS. For comparison of linearity, serially diluted recombinant hBDs were used. ELISA readings for hBD-3 using hBD-2 calibrators (A) and for hBD-2 using hBD-3 calibrators (B) are also incorporated (black squares).

Evaluation of ELISA for Detection of hBD-2 and -3 by Use of Different Capture and Detection Antibodies We investigated the sensitivity of commercially available antibodies against hBD-2 and hBD-3 (Table 1). Affinity-purified polyclonal capture antibodies (antihuman BD-2 and BD-3; Peprotech) and biotinylated anti-hBD detection antibodies (-2 and -3; Peprotech) provided the highest sensitivity in our ELISA formats. Using this pair of antibodies, absorbance at 415 nm against the respective calibrators (rh BD-2, 0.075-9.6 µg/L; rhBD-3, 3.0-192 µg/L) exhibited a linear correlation coefficient of r>0.99 for both defensins (FIG. 2). The limit of detection (limit of the blank) for the assay, defined as the mean of the buffer control (PBS)+3SD, was 75 ng/L for hBD-2 and 3 µg/L for hBD-3. We observed no cross-reactivity between the 2 defensin peptides (FIG. 2).

Detection of hBD-2 and -3 in: Saliva

Figure 3:
FIG. 3 illustrates a Western blot of hBD-3 in saliva. Whole saliva (100 μl) was centrifuged (10,000 g, 4° C., 10 min); supernatant was lyophilized, reconstituted in 20 μl of sample buffer, separated on 12% Tris-HCl gels (Bio-Rad) along with recombinant hBD-3 (50 ng; positive control), and transferred to a polyvinylidene difluoride membrane. The membrane was blocked with 5% skim milk in TBS containing 0.05% Tween for 1 h, followed by overnight incubation with anti-hBD-3 primary antibody (Peprotech). The membrane was washed, incubated with horseradish peroxidase-conjugated secondary antibody (Bio-Rad), and visualized with Supersignal West Femto Maximum Sensitivity Substrate (Pierce).

We and others have detected hBD-1 and hBD-2 in saliva using Western blot analysis (Sahasrabudhe et al., (2000) J. Dent. Res. 79:1669-1674; Mathews et al., (1999) Infect. Immun. 67:2740-2745). Here we demonstrate that Western blot analysis can detect hBD-3 in normal human saliva (FIG. 3). We analyzed samples from 3 healthy individuals. Both hBD-2 and -3 were detectable in all 3 samples. When serially diluted, saliva samples were used, however, nonlinearity in ELISA readouts for both hBDs was observed (FIG. 2), Linear correlation coefficient (r) values for both hBD-2 and hBD-3 were far lower than the values obtained with serially diluted recombinant hBDs (r>0.99). This non linearity led us to investigate the possibility of interference by other molecules present in saliva.

Masking Effect of Detection of hBD-2 and -3

Figure 4:
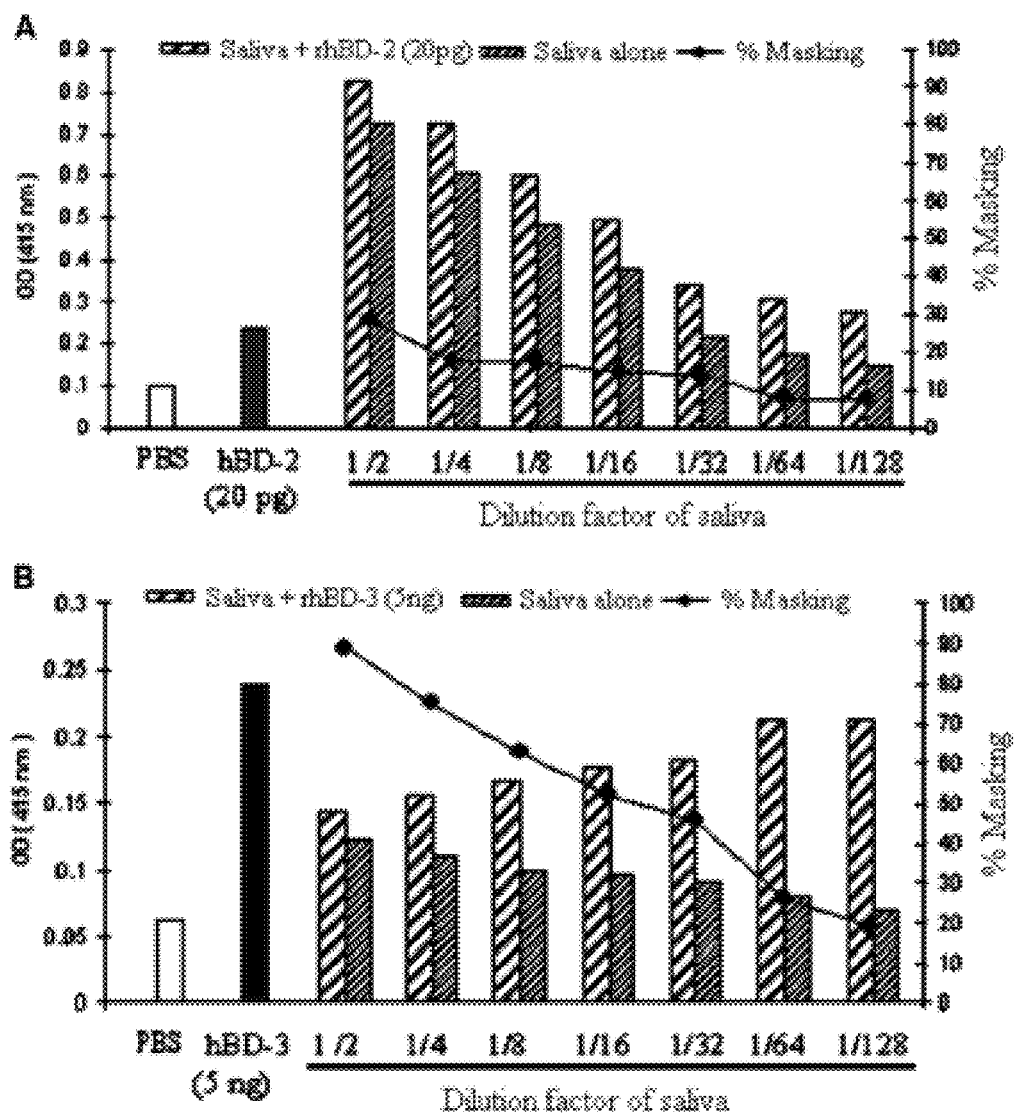
FIG. 4 illustrates graphs showing the masking effect of saliva in the detection of hBD-2 (A) and hBD-3 (B) using ELISA. Serially diluted (1:2 to 1:128 with PBS) saliva was enriched with recombinant hBDs (20 pg hBD-2 or 5 ng hBD-3), and percent masking of the respective hBDs in our ELISA was measured from absorbance readings of saliva enriched with hBDs and hBDs alone. The formula used was % masking=100%−(ASaliva+rhBDs−ASaliva)/(ArhBDs−Anegative control)×100], where A is absorbance. The absorbance reading of PBS was the negative control.

We performed ELISA measurements of pooled (n=3) serially diluted saliva (1:2 to 1:128), with or without addition of rhBD-2 (20 pg) or rhBD-3 (5 ng). We observed significantly lower detection of added hBDs in the presence of saliva compared with hBDs in PBS, even when the dilution was as low as 1:128. From the calculated percent masking, it became apparent that salivary masking of both hBDs decreased with increased dilution of the saliva, and that the percent masking of hBD-3 was greater than that of hBD-2 (FIG. 4). These results indicate that masking agents act differentially on the 2 defensin peptides.

Role of Mucin in Masking hBD-2 and -3 ELISA Signals

Figure 5:
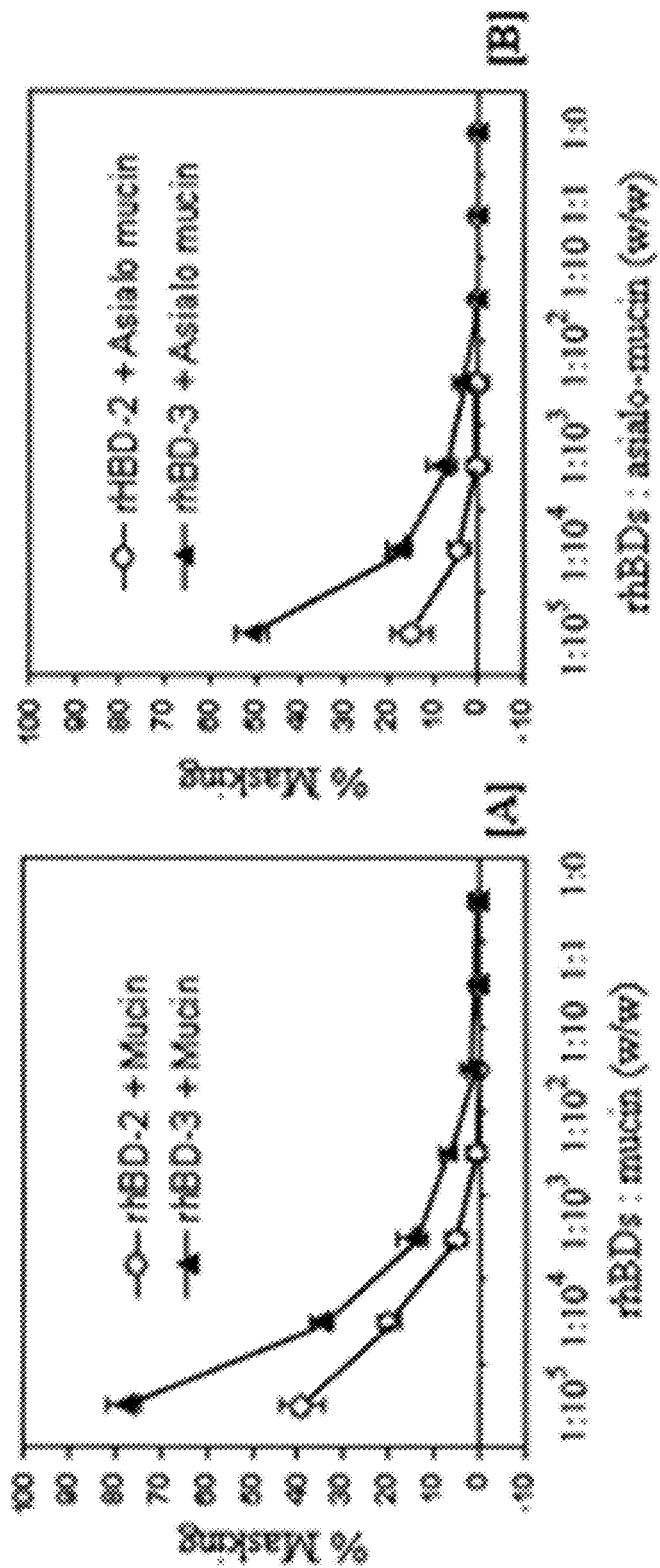
FIG. 5 illustrates plots showing the masking effect of mucins and asialo-mucins in the detection of hBDs using ELISA. Serially diluted mucin in PBS (A) or serially diluted asialo-mucin in PBS (B) was enriched with 20 pg rhBD-2 and 5 ng rhBD-3, respectively. The absorbance (A) of the positive control (20 pg for rhBD2' 5 ng for rhBD3) was set at 100% detection. The percent masking by either mucin or asialo-mucin was calculated by the following formula: % masking= [100%−(ArhBDs+mucins−Anegative control)/(ArhBDs−Anegative control)×100]. The absorbance reading of PBS was the negative control.

Because large anionic glycoproteins, i.e., mucins, are abundantly present in saliva (Rayment et al., (2000) J. Dent. Res. 79:1765-1762) and in other epithelial cell-derived body fluids (Gipson et al., (1997) Biol. Reprod. 56:999-1011; Thornton et al., (1997) 272:9561-9566), we conducted ELISAs of fixed concentrations of hBD-2 and -3 in the presence of serially diluted purified salivary mucins to determine the involvement of these molecules in masking hBD detection. Because the sensitivity of the two defensin assays varied, we used different fixed amounts of each, 20 pg hBD-2 and 5 ng hBD-3, and added purified mucin (OSM) in wt:wt ratios with the defensins (FIG. 5A). The results demonstrated concentration-dependent mucin-associated masking of hBD-2 and -3. To establish if anionic sialic acid residues of mucin are involved in the masking effect, we conducted ELISAs of hBDs in the presence of neuraminidase-treated mucin, i.e., asialo-mucin. FIG. 5B shows a decrease of ~25%-30% in masking of both hBDs by asialo-mucin compared with untreated mucin (FIG. 5A), confirming a role for sialic acid residues in masking hBD signals in the ELISAs.

Optimization of the ELISA for Detection of hBD-2 and -3 in Body Fluids

Figure 6:
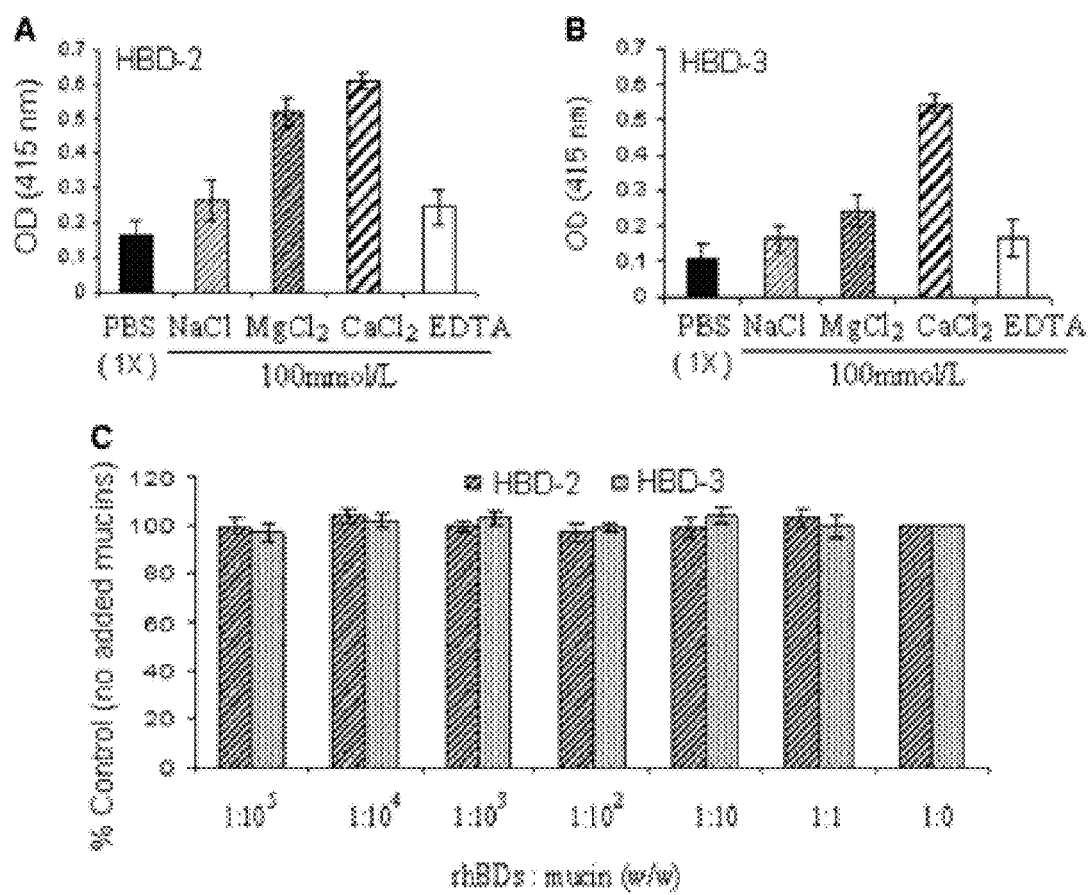
FIG. 6 illustrates graphs in (A) and (B) showing the effect of inorganic salts on ELISA readouts. A saliva sample was mixed (1:1) with respective inorganic salts (final concentration 100 mmol/L) as shown and 100 μL from each condition was used to screen hBD-2 and -3 concentrations by ELISA. Triplicate assays were performed and results are expressed as the mean and SE. In (C), ELISA readouts for hBD-2 and hBD-3 preincubated with serially diluted mucin and assayed in the presence of 250 mmol/L $CaCl_2$. HBDs and mucin were preincubated in 250 mmol/L $CaCl_2$, followed by the ELISA assay. The y axis represents the percent of ELISA readout obtained when comparing absorbance for hBDs in the presence or absence of mucin.
Figure 8:
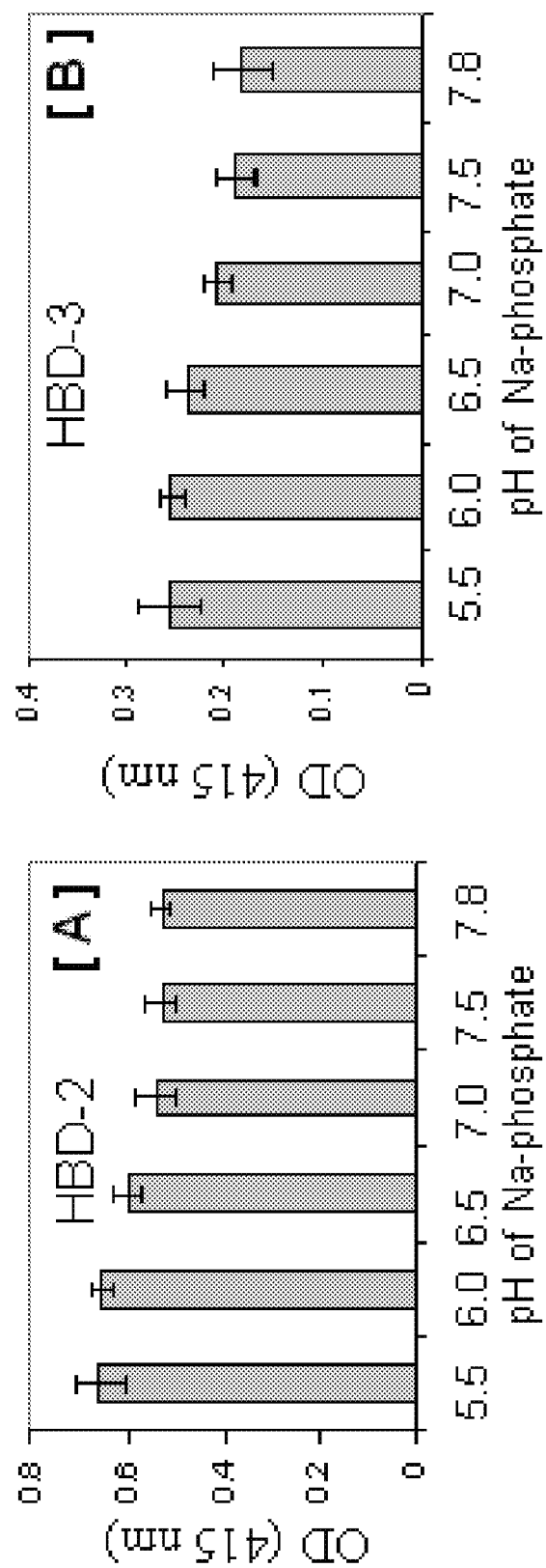
FIG. 8 illustrates graphs showing the effect of varying pH levels on the detection of hBD-2 (A), and hBD-3 (B). Pooled saliva sample (n=3) was mixed (1:1) with Na-phosphate buffer (final concentration 100 mmol/L) with the indicated pH range and HBD-2 & HBD-3 were determined by ELISA. Triplicate assays were performed and results are mean+SE.
Figure 9:
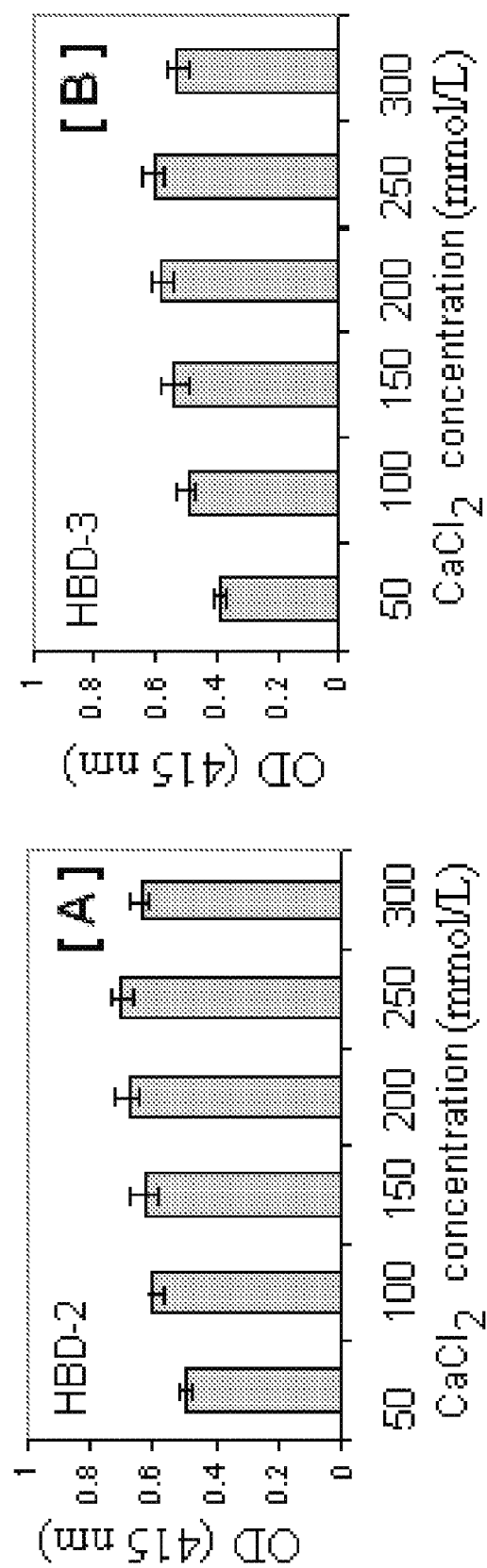
FIG. 9 illustrates graphs showing the effect of varying $CaCl_2$ concentrations on the detection of hBD-2 (A), and hBD-3 (B). Pooled saliva sample (n=3) was mixed (1:1) with increasing concentrations of $CaCl_2$ (50-300 mmol/L, final concentrations) and HBD-2 &-3 were determined by ELISA. Triplicate assays were performed and results are mean+SE.

We explored different strategies to overcome the masking. We examined the effect of pH on the detection of hBDs in saliva by assaying a pooled saliva sample (n=3) using a pH interval of 5.5-7.8 using 100 mmol/L sodium phosphate. Detection of the salivary hBDs was slightly better in acidic pH, but acidic pH alone did not improve hBD detection in saliva to any significant degree (see FIG. 8). We then examined the effect of monovalent and divalent cations at various ionic strengths on the ELISAs to detect hBDs in saliva. We found that divalent cations ($Mg^{2+}$, $Ca^{2+}$) were better than monovalent cations ($Na^+$) (FIG. 6) and that 250 mmol/L $CaCl_2$ optimized the detection of both hBD-2 and hBD-3 equally well (see FIG. 9). We further compared the ELISA signals from neuraminidase-pretreated saliva in PBS to the ELISA signals from saliva in 250 mmol/L $CaCl_2$ and observed that 250 mmol/L $CaCl_2$ was best at enhancing the hBD-2 and hBD-3 signals.

Indeed, when purified mucin was incubated with the respective hBDs in the presence of 250 mmol/L $CaCl_2$, we were able to detect hBD-2 and -3 to virtually 100% (FIG. 6C). We therefore performed subsequent ELISA assays for detection of hBDs in body fluids in the presence of 250 mmol/L $CaCl_2$.

Intra- and Interassay Precision

Using the hBD-2 calibrator (1 µg/L) and pooled saliva (8.2 µg/L hBD-2), the intraassay CVs were 4.8% and 6.06%, respectively (n=20), and interassay CVs were 5.81% and 7.63%, respectively (n=8). With an hBD-3 calibrator (50 µg/L) and the pooled saliva (627 µg/L hBD-3), the intraassay CVs were 4.6% and 6.7%, respectively (n=20), and the interassay CVs were 5.31% and 8.12%, respectively.

Analytical Recovery of the Calibrator

Recoveries of exogenously added recombinant hBD-2 (50, 100, and 200 ng/L.) from saliva, BF, BAL, and CVL samples ranged from 82%-107%, 88%-105%, 81%-107%, and 84%-103%, respectively. The percentage recoveries of exogenously added recombinant hBD-3 (2.5. 5, and 10 µg/L) from saliva, SF, BAL. and CVL samples ranged from 89% to 104%, 83% to 99%, 86% to 109%, and 87% to 107%, respectively.

Measurement of hBD-2 and -3 Concentrations in Saliva from Healthy Individuals

Figure 7:
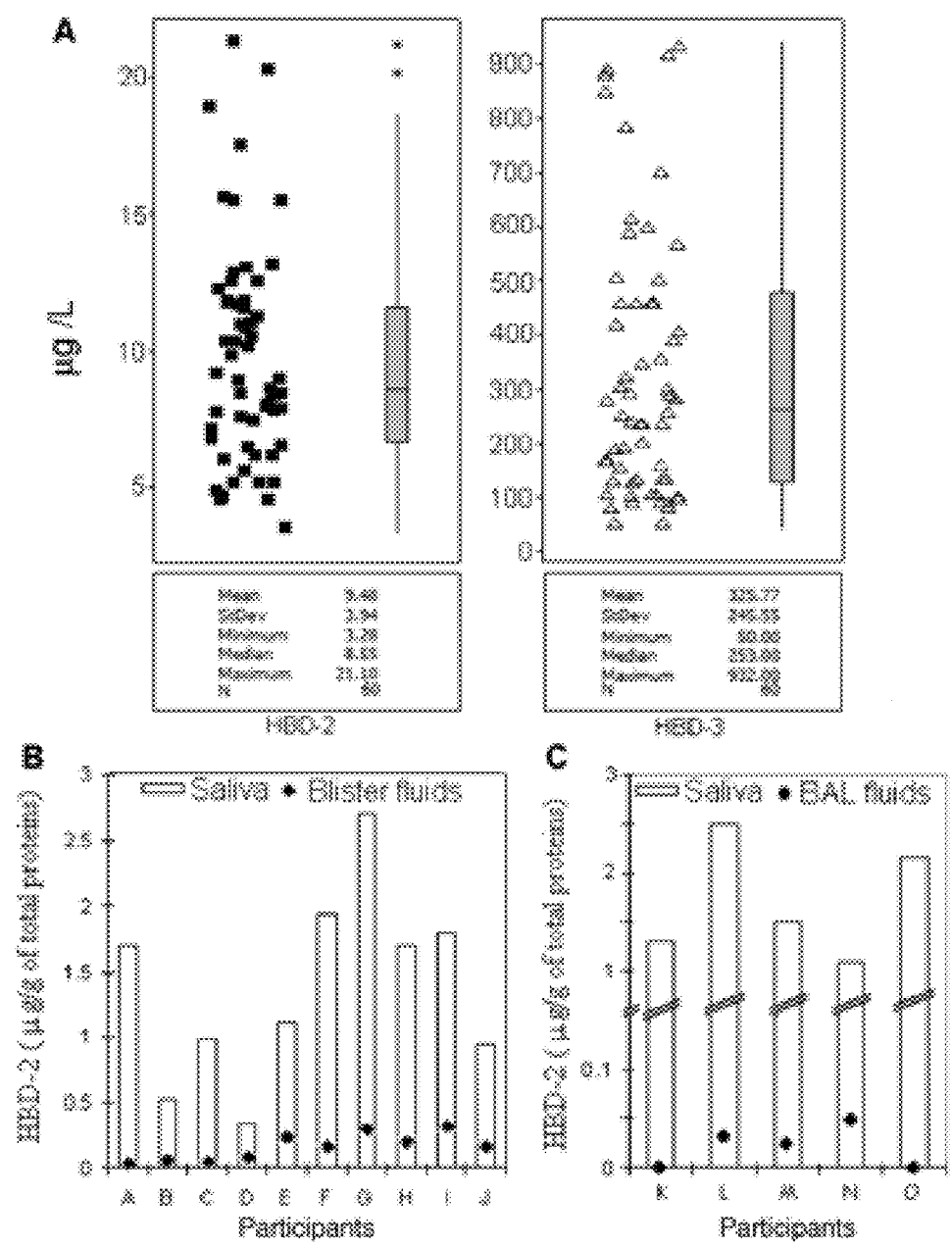
FIG. 7 illustrates in (A), a box-plot representation of salivary hBD-2 and hBD-3 peptide concentrations in healthy participants (n=60). Each saliva sample was mixed (1:1) with $CaCl_2$ (final concentration 250 mmol/L), and 100 μL from each sample was assayed for the presence of the respective hBD. Each sample was run in duplicate. Results were obtained by running hBD-2 and hBD-3 calibrators with each assay, respectively. A * indicates outliers. (B), ELISA measurements of hBD-2 concentrations in BFs (n=10) and matched saliva from healthy donors. BF (75 μL) from each sample was mixed with 25 μL $CaCl_2$ (final concentration 250 mmol/L) and assayed for hBD-2. (C), determination of hBD-2 in BAL (n=5) samples and matched saliva from healthy donors. BAL samples were lyophilized, dialyzed, and reconstituted in 250 mmol/L $CaCl_2$, and 100 μL from each sample was assayed for hBD-2. Salivary hBD-2 was measured as described (A). Results are calculated as the ratio of hBD-2 peptide compared with total protein (measured by Bio-Rad Dc Protein Assay) per sample.

Saliva from 60 healthy individuals was analyzed for the presence of hBD-2 and -3. Concentrations of hBD-2 ranged from 1.2 to 21.1 µg/L (mean, 9.48; median. 3.28), whereas concentrations of hBD-3 ranged from 50 to 931 µg/L (mean, 325.77; median, 253) (FIG. 7A).

Identification of hBD Concentrations in Blister Fluids, BAL, Vaginal Swabs, and CVL from Healthy Individuals We analyzed BF samples from healthy participants (n=10) by ELISA for the presence of both hBD-2 and hBD-3 peptides. Although we could not detect hBD-3 in the BF samples (limit of detection of assay, 3.0 µg/L). We found hBD-2 in all the samples (30-320 ng/g total protein). The hBD-2 concentrations (in µg/g total BF proteins) in BF were then compared with salivary hBD-2 concentrations (in µg/g total salivary proteins) from corresponding samples (FIG. 7B). BF concentrations of hBD-2 did not correlate with the salivary concentrations of hBD-2 peptides. Similar analysis of the hBDs in BAL from healthy participants (n=5) showed the absence of hBD-3 and low concentrations of hBD-2 (0-49 ng/s total proteins). We also compared the concentration of hBD-2 in BAL with that in corresponding saliva samples (FIG. 7C). BAL concentrations of hBD-2 also did not correlate with the salivary hBD-2 peptide concentrations. Unlike BF and BAL, we could detect hBD-3, along with hBD-2, in CVL and vaginal swabs from healthy women (n=2; mean hBD-2 in CVL, 1.42 µ/g total proteins: in vaginal swab, 3.42 µg/g total proteins; mean hBD-3 in CVL, 55 µg total proteins. in vaginal swab. 103 µ/g total proteins).

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method of detecting β-defensin in a bodily sample of a subject comprising:
   obtaining a bodily sample from the subject;
   reducing the electrostatic interaction between β-defensin and negatively charged moieties in the bodily sample;
   contacting the bodily sample with a capture antibody or an epitope binding fragment thereof, the capture antibody or an epitope binding fragment thereof being immunoreactive with and binding to the β-defensin; and
   detecting bound β-defensin in the bodily sample.

2. The method of claim 1, the step of detecting bound β-defensin captured comprising:
   contacting the bound β-defensin with a detection antibody or epitope binding fragment thereof, the detection antibody or epitope binding fragment thereof being coupled to a detectable label; and
   detecting the detectable label in the bodily sample.

3. The method of claim 1, the step of reducing the electrostatic interaction between β-defensin and negatively charged moieties in the sample comprising adding positively charged moieties to the bodily sample at an amount effective to reduce the electrostatic interactions between β-defensin and negatively charged moieties in the bodily sample.

4. The method of claim 3, the positively charged moieties comprising cations.

5. The method of claim 4, the cations being selected from the group consisting of $Mg^{2+}$, $Ca^{2+}$, and combinations thereof.

6. The method of claim 1, wherein the electrostatic interactions are reduced by administering about 50 mmol/L to about 500 mmol/L of $CaCl_2$ to the bodily sample.

7. The method of claim 2, the detectable label being used to quantify the amount of β-defensin in the sample.

8. The method of claim 1, the bodily sample comprising a bodily fluid.

9. The method of claim 8, the bodily fluid selected from the group consisting of saliva, genital secretions, cervicovaginal lavage, bronchoalveolar lavage, blister fluid, and combinations thereof.

10. A method of quantifying β-defensin in a bodily sample of a subject comprising:
    obtaining a bodily sample from the subject;
    reducing the electrostatic interaction between β-defensin and negatively charged moieties in the bodily sample;
    contacting the bodily sample with a capture antibody or an epitope binding fragment thereof, the capture antibody or an epitope binding fragment thereof being immunoreactive with the β-defensin;
    contacting the bound β-defensin with a detection antibody or epitope binding fragment thereof, the detection antibody or epitope binding fragment thereof being coupled to a detectable label;
    detecting the detectable label in the sample; and
    correlating the amount of detectable label in the sample to an amount of β-defensin in the bodily sample.

11. The method of claim 10, the step of reducing the electrostatic interaction between β-defensin and negatively charged moieties in the sample comprising adding positively charged moieties to the bodily sample at an amount effective to reduce the electrostatic interactions between β-defensin and negatively charged moieties in the bodily sample.

12. The method of claim 11, the positively charged moieties comprising cations.

13. The method of claim 12, the cations being selected from the group consisting of $Mg^{2+}$, $Ca^{2+}$, and combinations thereof.

14. The method of claim 10, wherein the electrostatic interactions are reduced by administering about 50 mmol/L to about 500 mmol/L of $CaCl_2$ to the bodily sample.

15. The method of claim 10, the bodily sample comprising a bodily fluid.

16. The method of claim 15, the bodily fluid selected from the group consisting of saliva, genital secretions, cervicovaginal lavage, bronchoalveolar lavage, blister fluid, and combinations thereof.

17. A method of quantifying β-defensin in a bodily sample from a subject comprising:
    obtaining a bodily sample from the subject;
    adding $CaCl_2$ to the bodily sample at an amount effective to reduce electrostatic interaction between β-defensin and negatively charged moieties in the bodily sample
    contacting the bodily sample with a capture antibody or an epitope binding fragment thereof, the capture antibody or an epitope binding fragment thereof being immunoreactive with the β-defensin;
    contacting the bound β-defensin with a detection antibody or epitope binding fragment thereof, the detection antibody or epitope binding fragment thereof being coupled to a detectable label;
    detecting the detectable label in the bodily sample; and
    correlating the amount of detectable label in the sample to an amount of β-defensin in the bodily sample.

18. The method of claim 17, the detection antibody or epitope binding fragment thereof being biotinylated.

19. The method of claim 17, the bodily sample comprising bodily fluid.

20. The method of claim 19, the bodily fluid selected from the group consisting of saliva, genital secretions, cervicovaginal lavage, bronchoalveolar lavage, blister fluid, and combinations thereof.

* * * * *